US009251779B2

(12) United States Patent
Asao et al.

(10) Patent No.: US 9,251,779 B2
(45) Date of Patent: Feb. 2, 2016

(54) NOISE REDUCTION APPARATUS

(71) Applicant: Panasonic Corporation, Osaka (JP)

(72) Inventors: Yoshifumi Asao, Osaka (JP); Tsuyoshi Maeda, Hyogo (JP)

(73) Assignee: Panasonic Intellectual Property Management Co., Ltd., Osaka (JP)

(*) Notice: Subject to any disclaimer, the term of this patent is extended or adjusted under 35 U.S.C. 154(b) by 408 days.

(21) Appl. No.: 13/748,924

(22) Filed: Jan. 24, 2013

(65) Prior Publication Data

US 2013/0188800 A1 Jul. 25, 2013

(30) Foreign Application Priority Data

Jan. 25, 2012 (JP) ................................. 2012-012700

(51) Int. Cl.
*A61F 11/06* (2006.01)
*G10K 11/16* (2006.01)
*G10K 11/178* (2006.01)

(52) U.S. Cl.
CPC .............. *G10K 11/16* (2013.01); *G10K 11/178* (2013.01); *G10K 2210/1281* (2013.01); *G10K 2210/1283* (2013.01); *G10K 2210/3016* (2013.01); *G10K 2210/3214* (2013.01)

(58) Field of Classification Search
CPC .................... G10K 11/178; G10K 2210/1281; G10K 2210/1283; G10K 2210/3016; G10K 11/16; G10K 2210/3214
USPC ............................ 381/71.1–71.12, 94.1–94.9
See application file for complete search history.

(56) References Cited

U.S. PATENT DOCUMENTS

2008/0317254 A1* 12/2008 Kano ................. G10K 11/1786 381/71.4
2011/0007907 A1* 1/2011 Park ..................... G10K 11/178 381/71.8

FOREIGN PATENT DOCUMENTS

| | | |
|---|---|---|
| JP | 2-285799 | 11/1990 |
| JP | 6-259086 | 9/1994 |
| JP | 7-253788 | 10/1995 |
| JP | 07253788 A * | 10/1995 |
| JP | 11-24670 | 1/1999 |

* cited by examiner

*Primary Examiner* — Vivian Chin
*Assistant Examiner* — Ammar Hamid
(74) *Attorney, Agent, or Firm* — Wenderoth, Lind & Ponack, L.L.P.

(57) ABSTRACT

A noise reduction apparatus includes a noise reduction amount calculator. The noise reduction amount calculator includes a difference calculator that obtains a difference between a level of the noise detected by a first noise detecting microphone and a level of the noise detected by a second noise detecting microphone when control sound is not output, a storage unit that stores the difference, an estimated noise value calculator that estimates a noise level that is to be detected by the second noise detecting microphone when the control sound is output, based on the level of the noise detected by the first noise detecting microphone when the control sound is output and the difference, and a reduction amount calculator that calculates a noise reduction amount on the noise reduction target position, based on the estimated noise value and the level of the noise detected by the second noise detecting microphone when the control sound is output.

9 Claims, 9 Drawing Sheets

NOISE REDUCTION APPARATUS

BACKGROUND

1. Technical Field

The present disclosure relates to a noise reduction apparatus for reducing noises.

2. Related Art

JP-A-2-285799 (Patent Document 1) discloses a basic configuration of a noise reduction apparatus. This noise reduction apparatus outputs a control sound of which phase is opposite to a noise from a noise source in a noise reduction position (control point). As a result, noises at the control point are reduced.

JP-A-7-253788 (Patent Document 2) discloses a noise reduction apparatus that estimates a noise reduction amount and controls an ON/OFF state of the noise reduction apparatus according to the estimated noise reduction amount. Specifically, the noise reduction apparatus has a speaker for outputting a control sound, a first microphone provided on a noise source side of the speaker, and a second microphone provided on an opposite noise source side (for example, the control point) of the speaker. The noise reduction apparatus detects a noise when the noise source operates and a noise (dark noise) when neither the noise source nor the noise reduction apparatus operates through the respective microphones, and estimates the noise reduction amount based on the detected noises. The noise reduction apparatus controls the ON/OFF state of the noise reduction apparatus according to the estimated noise reduction amount.

SUMMARY

A noise reduction apparatus according to the present disclosure includes a first noise detecting microphone operable to detect a noise on a position different from a noise reduction target position, a second noise detecting microphone operable to detect a noise on the noise reduction target position, a control sound output unit operable to generate a control sound for reducing the noise on the noise reduction target position based on an output from the first noise detecting microphone and an output from the second noise detecting microphone to output the control sound, and a noise reduction amount calculator operable to calculate a reduction amount of the noise on the noise reduction target position based on the output from the first noise detecting microphone and the output from the second noise detecting microphone. The noise reduction amount calculator includes a difference calculator operable to obtain a difference between a level of the noise detected by the first noise detecting microphone and a level of the noise detected by the second noise detecting microphone in a state where the control sound output unit does not output the control sound, a storage unit operable to store the difference calculated by the difference calculator, an estimated noise value calculator operable to estimate a noise level that is to be detected by the second noise detecting microphone in the state where the control sound output unit does not output the control sound, based on the level of the noise detected by the first noise detecting microphone in a state where the control sound output unit outputs the control sound and the difference stored in the storage unit, and a reduction amount calculator operable to calculate a noise reduction amount on the noise reduction target position, based on the estimated noise value calculated by the estimated noise value calculator and the level of the noise detected by the second noise detecting microphone in the state where the control sound output unit outputs the control sound.

The noise reduction apparatuses of Patent Documents 1 and 2 occasionally give uncomfortable feelings to users during a noise reduction operation.

The present disclosure provides a noise reduction apparatus capable of reducing uncomfortable feelings to be given to users during an operation of the noise reduction apparatus.

The noise reduction apparatus of the present disclosure can reduce an uncomfortable feeling to be given to a user during a noise reduction operation.

DETAILED DESCRIPTION OF PREFERRED EMBODIMENTS

Figure 1:
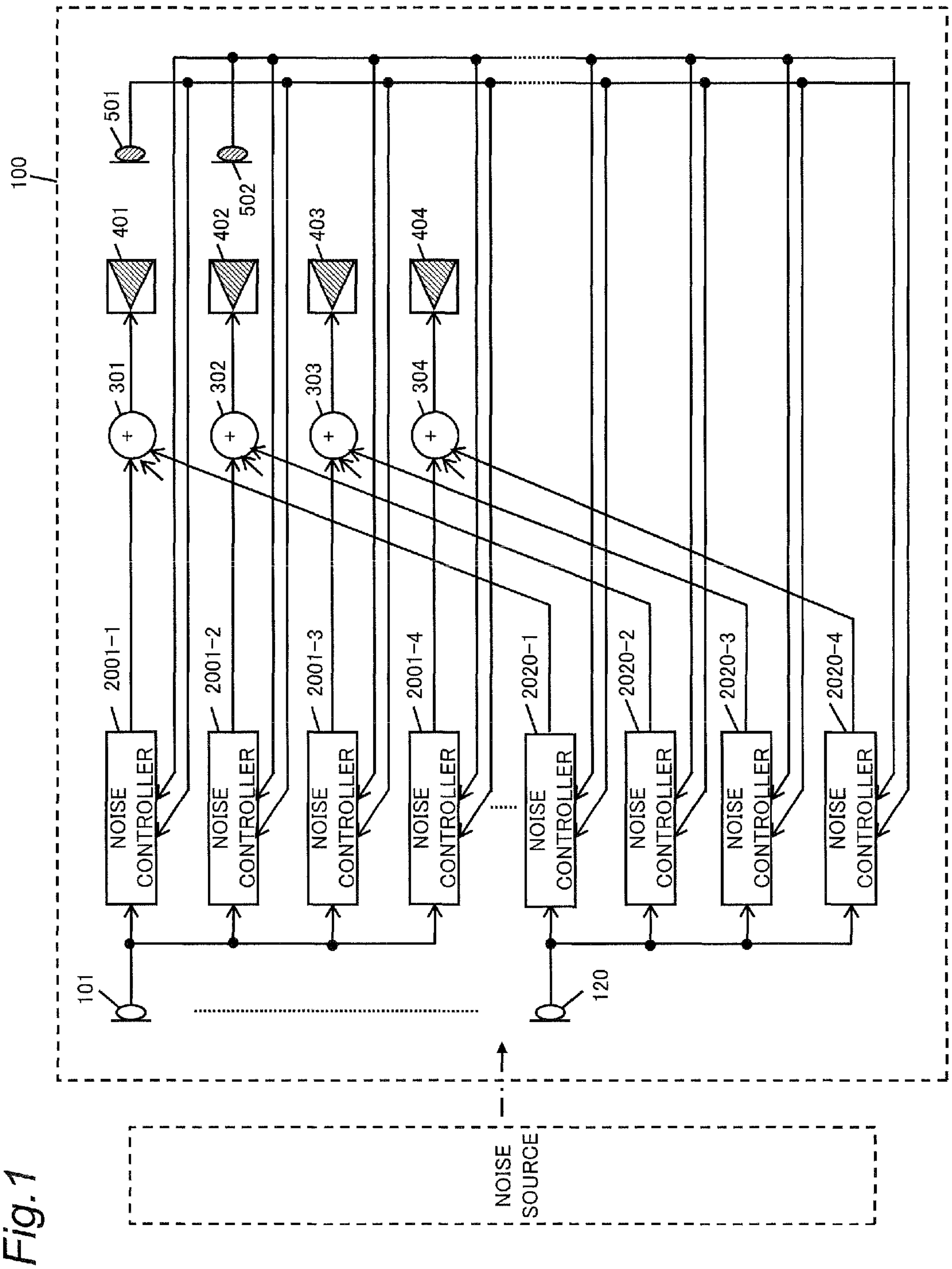
FIG. 1 is a block diagram illustrating a basic configuration illustrating a noise reduction apparatus according to a first embodiment.

Embodiments will be described in detail below with reference to the drawings as necessary. Description that is more detailed than necessity will be occasionally omitted. For example, detailed description about already well-known matters and overlapped description about substantially identical configurations will be occasionally omitted. This is for avoiding the following description from being more redundant than necessity and making understanding of those skilled in the art easy.

The inventors provide the accompanying drawings and the following description in order to have those skilled in the art sufficiently understand the present disclosure, and thus the disclosure is not intended to limit the subject matter described in the claims.

BACKGROUND OF THE PRESENT DISCLOSURE

Before a noise reduction apparatus according to the present embodiment is described, the background of the present disclosure is described.

For example, in aircraft and railway vehicles, information such as voice service is provided to users who have taken their seats. For this reason, noises at the seats become a problem.

Examples of noises in the aircraft are noises generated from devices for producing a thrust force, such as an engine and a propeller, and noises relating to aerial flow of a wind noise generated according to transfer of aircraft through airspace. Such noises generated from respective noise sources are transmitted into a cabin of the aircraft, and give an uncomfortable feeling to the passenger and interfere with the voice service.

In order to reduce noises in the cabin of the aircraft, noise insulation materials (passive damping unit) such as barrier materials and absorbers are conventionally arranged between the cabin and the noise sources.

However, countermeasures against the noises using the noise insulation materials cause the following problems. That is, the barrier materials and the absorbers generally have high-density. Such high-density materials cause an increase in weight of the aircraft. The increase in weight causes deterioration in fuel efficiency and decrease in a flight range, and leads to deteriorations in economic efficiency and functions of the aircraft. The barrier materials and the absorbers are easily damaged, and thus these structural materials have a problem in strength. Further, they have a problem in that a design such as texture is deteriorated.

In order to cope with these problems, in recent years, there is proposed an active attenuation unit for outputting control sounds of which phase is opposite to noises from noise sources at a control point to reduce the noises at the control point. Examples of the active attenuation unit are described in Patent Documents 1 and 2.

However, the noise reduction apparatuses in Patent Documents 1 and 2 occasionally give uncomfortable feelings to users during the operation of the noise reduction apparatuses as described above.

Specifically, noises from noise sources may occasionally fluctuate. When the fluctuation in noises occurs, in the noise reduction apparatus of Patent Document 1, noises from the noise sources and control sounds occasionally have the same phase, and thus noises at the control point occasionally increase. That is, noises cannot be reduced, thereby giving uncomfortable feelings to the users.

In the noise reduction apparatus of Patent Document 2, ON/OFF control of the noise reduction apparatus can be made according to a noise reduction amount. However, when the noise reduction amount is obtained, a noise value on a position of a second microphone that is generated when the noise sources operate and the noise reduction apparatus is stopped should be obtained. For this reason, the noise reduction apparatus is required to be stopped at a constant cycle. While the noise reduction apparatus is stopped, noises from the noise sources are transmitted directly. As a result, uncomfortable feelings may be given to the users.

The present disclosure adopts the following configuration in order to solve above problem.

The noise reduction apparatus according to embodiments will be described below with reference to the drawings.

First Embodiment

1. Configuration

1-1. Configuration of Noise Reduction Apparatus

The first embodiment will describe a case where the noise reduction apparatus of the present disclosure is installed in seats of the aircraft.

Figure 2C:
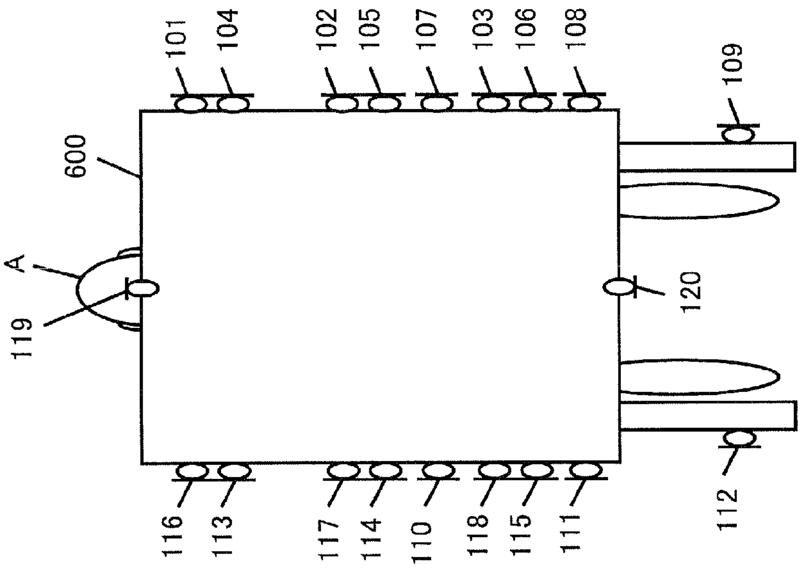
FIGS. 2A to 2C are diagrams illustrating a seat where the noise reduction apparatus is installed.
Figure 2B:
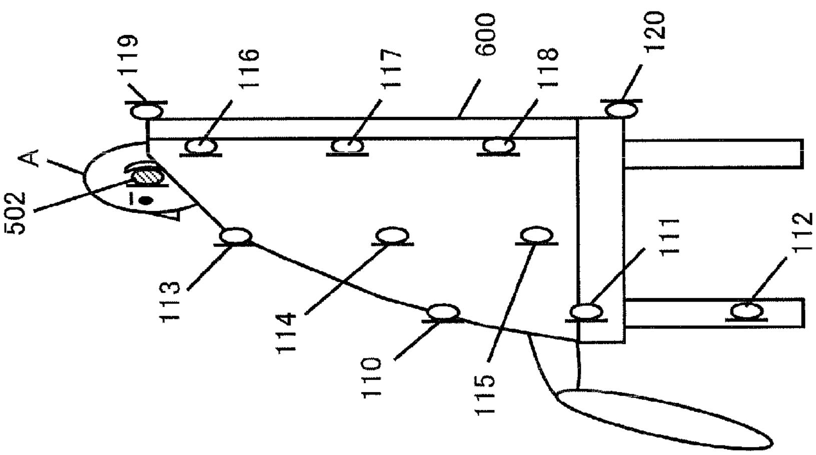
Figure 2A:
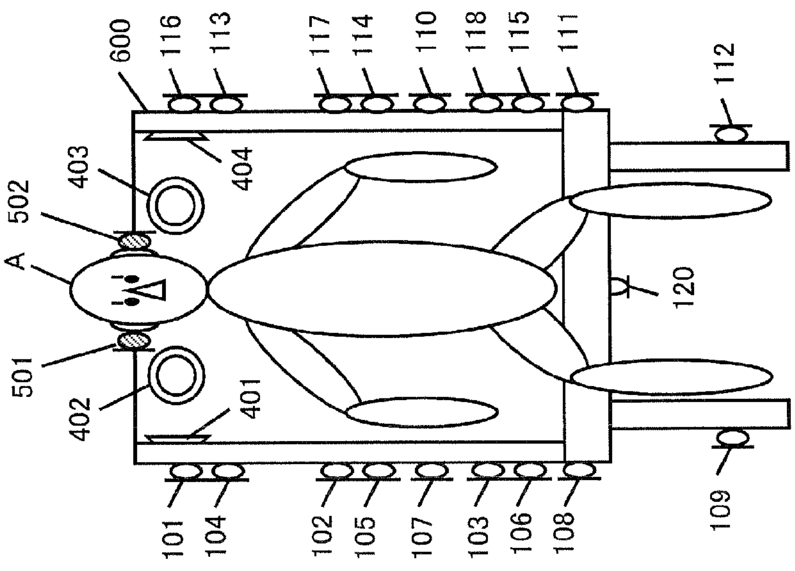

FIG. 1 is a block diagram illustrating a basic configuration of the noise reduction apparatus according to the first embodiment. FIGS. 2A to 2C are diagrams illustrating a seat where the noise reduction apparatus according to the first embodiment is installed. Specifically, FIG. 2A is a front view of the seat. FIG. 2B is a side view of the seat. FIG. 2C is a rear view of the seat.

As shown in FIG. 1, a noise reduction apparatus 100 includes noise detecting microphones 101 to 120, noise controllers 2001-1 to 2020-1, 2001-2 to 2020-2, 2001-3 to 2020-3, and 2001-4 to 2020-4, adders 301 to 304, control speakers 401 to 404, and residual noise detecting microphones 501 and 502.

As shown in FIGS. 2A to 2C, the noise detecting microphones 101 to 120 are decentrally arranged on a side portion and the like of a seat 600, and detect noises from a circumference of the seat 600.

The residual noise detecting microphones 501 and 502 are arranged at ears of a user A. In the first embodiment, positions of the ears of the user A are set as control points.

The control speakers 401 to 404 are arranged on positions located above the seat 600, which is near the ears of the user (passenger) A and at approximately the same height as the ears.

Returning to FIG. 1, the noise detecting microphones 101 to 120 detect the noises generated from noise sources, and convert the noises into electric signals to output the signals.

The residual noise detecting microphones 501 and 502 detect residual noises at the control points.

The noise controllers 2001-1 to 2020-1, 2001-2 to 2020-2, 2001-3 to 2020-3, and 2001-4 to 2020-4 generate control sound signals based on noise signals from the noise detecting microphones 101 to 120 and residual noise signals from the residual noise detecting microphones 501 and 502 so that levels of the residual noises detected by the residual noise detecting microphones 501 and 502 are minimum. That is, the noise controllers perform feedback control. As a result, even when a noise environment changes, the noise level on positions near the ears of the user A can be minimum.

The adder 301 adds the control sound signals output from the noise controllers 2001-1 to 2020-1, and outputs the added signal to the control speaker 401. The adder 302 adds control sound signals output from the noise controllers 2001-2 to 2020-2, and outputs the added signal to the control speaker 402. The adder 303 adds control sound signals output from the noise controllers 2001-3 to 2020-3, and outputs the added signal to the control speaker 403. The adder 304 adds control sound signals output from the noise controllers 2001-4 to 2020-4, and outputs the added signal to the control speaker 404.

The control speaker 401 converts the control sound signal from the adder 301 into a sound wave, and outputs the sound wave. The control speaker 402 converts the control sound signal from the adder 302 into a sound wave, and outputs the sound wave. The control speaker 403 converts the control sound signal from the adder 303 into a sound wave, and outputs the sound wave. The control speaker 404 converts the control sound signal from the adder 304 into a sound wave, and outputs the sound wave.

When the control sound is output from the control speaker 401, the residual noise detecting microphones 501 and 502 at the control points detect noises (residual noises) that are generated by interference between noises from the noise sources and the control sound from the control speaker 401. For example, when the noises from the noise sources and the control sound from the control speaker 401 have opposite phases at the control points, the residual noise detecting microphones 501 and 502 detect residual noises of which levels are lower than that of the noises from the noise sources. When the noises and the control sound have the same phase at the control points, the residual noise detecting microphones 501 and 502 detect residual noises of which levels are higher than the levels of the noises from the noise sources. When the control sound is not output from the control speaker 401, the residual noise detecting microphones 501 and 502 at the control points detect the noises transmitted from the noise sources as residual noises.

The residual noise signals from the residual noise detecting microphones 501 and 502 are input into the noise controllers 2001-1 to 2020-1, 2001-2 to 2020-2, 2001-3 to 2020-3, and 2001-4 to 2020-4, respectively. The noise controllers perform feedback with respect to a result of the operation of the noise reduction apparatus 100.

The operation of the noise reduction apparatus 100 will be described in detail below.

The noise signal from the noise detecting microphone 101 is output to the noise controllers 2001-1 to 2001-4. The noise signal from the noise detecting microphone 102 is output to the noise controllers 2002-1 to 2002-4. Similarly, the noise signals from the noise detecting microphones 103 to 120 are output to the noise controllers 2003-1 to 2003-4, 2004-1 to 2004-4, . . . 2020-1 to 2020-4, respectively.

A transfer function at the time when a sound wave is transferred from the control speaker 401 to the residual noise detecting microphone 501, and a transfer function at the time when a sound wave is transferred from the control speaker 401 to the residual noise detecting microphone 502 are set in the noise controller 2001-1. The transfer functions are set by using, for example, Filtered-X_LMS method.

The noise controller 2001-1 obtains a filter coefficient that is applied to an adaptive filter in the noise controller 2001-1 using the set transfer functions. At this time, the noise controller 2001-1 obtains the filter coefficient that makes the levels of the residual noise signals output from the residual noise detecting microphones 501 and 502 minimum. The noise controller 2001-1 updates a current filter coefficient based on the newly obtained filter coefficient.

Similarly to the noise controller 2001-1, a transfer function at the time when a sound wave is transferred from the control speaker 401 to the residual noise detecting microphone 501, and a transfer function at the time when a sound wave is transferred from the control speaker 401 to the residual noise detecting microphone 502 are set in the noise controller 2002-1. The noise controller 2002-1 obtains a filter coefficient to be applied to an adaptive filter in the noise controller 2002-1. At this time, the noise controller 2002-1 obtains the filter coefficient for making the residual noise signals output from the residual noise detecting microphones 501 and 502 minimum. The noise controller 2002-1 updates a current filter coefficient based on the newly obtained filter coefficient.

Similarly, in the noise controllers 2003-1 to 2020-1, a transfer function at the time when a sound wave is transferred from the control speaker 401 to the residual noise detecting microphone 501, and a transfer function at the time when a sound wave is transferred from the control speaker 401 to the residual noise detecting microphone 502 are set. The noise controllers 2003-1 to 2020-1 obtain filter coefficients to be applied to adaptive filters in the noise controllers 2003-1 to 2020-1. At this time, the noise controllers 2003-1 to 2020-1 obtain the filter coefficients for making the residual noise signals output from the residual noise detecting microphones 501 and 502 minimum. The noise controllers 2003-1 to 2020-1 update current filter coefficients based on the newly obtained filter coefficients.

In the noise controllers 2001-2 to 2020-2, a transfer function at the time when a sound wave is transferred from the control speaker 402 to the residual noise detecting microphone 501, and a transfer function at the time when a sound wave is transferred from the control speaker 402 to the residual noise detecting microphone 502 are set. The noise controllers 2001-2 to 2020-2 obtain the filter coefficients to be applied to adaptive filters in the noise controllers 2001-2 to 2020-2. At this time, the noise controllers 2001-2 to 2020-2 obtain the filter coefficients for making the residual noise signals output from the residual noise detecting microphones 501 and 502 minimum. The noise controllers 2001-2 to 2020-2 update current filter coefficients based on the newly obtained filter coefficients.

In the noise controllers 2001-3 to 2020-3, a transfer function at the time when a sound wave is transferred from the control speaker 403 to the residual noise detecting microphone 501, and a transfer function at the time when a sound wave is transferred from the control speaker 403 to the residual noise detecting microphone 502 are set. The noise controllers 2001-3 to 2020-3 obtain filter coefficients to be applied to adaptive filters in the noise controllers 2001-3 to 2020-3. At this time, the noise controllers 2001-3 to 2020-3 obtain the filter coefficients for making the residual noise signals output from the residual noise detecting microphones 501 and 502 minimum. The noise controllers 2001-3 to 2020-3 update current filter coefficients based on the newly obtained filter coefficients.

In the noise controllers 2001-4 to 2020-4, a transfer function at the time when a sound wave is transferred from the control speaker 404 to the residual noise detecting microphone 501, and a transfer function at the time when a sound wave is transferred from the control speaker 404 to the residual noise detecting microphone 502 are set. The noise controllers 2001-4 to 2020-4 obtain the filter coefficients to be applied to adaptive filters in the noise controllers 2001-4 to 2020-4. At this time, the noise controllers 2001-4 to 2020-4 obtain filter coefficients for making the residual noise signals output from the residual noise detecting microphones 501 and 502 minimum. The noise controllers 2001-4 to 2020-4 update current filter coefficient based on the newly obtained filter coefficients.

The noise controllers 2001-1 to 2020-1 give signal processes to the input noise signals, respectively, using the updated filter coefficients to generate control sound signals, and output the generated control sound signals to the adder 301. The adder 301 adds the control sound signals output from the noise controllers 2001-1 to 2020-1, and outputs the added signal to the control speaker 401. The control speaker 401 outputs the control sound to the control point based on the control sound signal from the adder 301.

The noise controllers 2001-2 to 2020-2 give signal processes to the input noise signals, respectively, using the updated filter coefficients to generate control sound signals, and output the generated control sound signals to the adder 302. The adder 302 adds the control sound signals output from the noise controllers 2001-2 to 2020-2, and outputs the added signal to the control speaker 402. The control speaker 402 outputs the control sound to the control point based on the control sound signal from the adder 302.

The noise controllers 2001-3 to 2020-3 give signal processes to the input noise signals, respectively, using the updated filter coefficients to generate control sound signals, and output the generated control sound signals to the adder 303. The adder 303 adds the control sound signals output from the noise controllers 2001-3 to 2020-3 to output the added signal to the control speaker 403. The control speaker 403 outputs a control sound to the control point based on the control sound signal from the adder 303.

The noise controllers 2001-4 to 2020-4 give signal processes to the input noise signals, respectively, using the updated filter coefficients to generate control sound signals, and output the generated control sound signals to the adder 304. The adder 304 adds the control sound signals output from the noise controllers 2001-4 to 2020-4, and outputs the added signal to the control speaker 404. The control speaker 404 outputs a control sound to the control point based on the control sound signal from the adder 304.

The feedback control is performed by the above processes so that the residual noises after the noise reduction become minimum. As a result, the noises at the control point, namely, at the ears of the user A can be reduced.

The first embodiment describes the case of using the adaptive filters, but when fluctuations in a frequency and a level of noises hardly occur or are small, fixed-type filters may be used. Also in this case, the noise reduction effect can be obtained.

1-2. Configuration of Noise Controller

Configurations of the noise controllers 2001-1 to 2001-4, 2002-1 to 2002-4, . . . 2020-1 to 2020-4 will be described.

Figure 3:
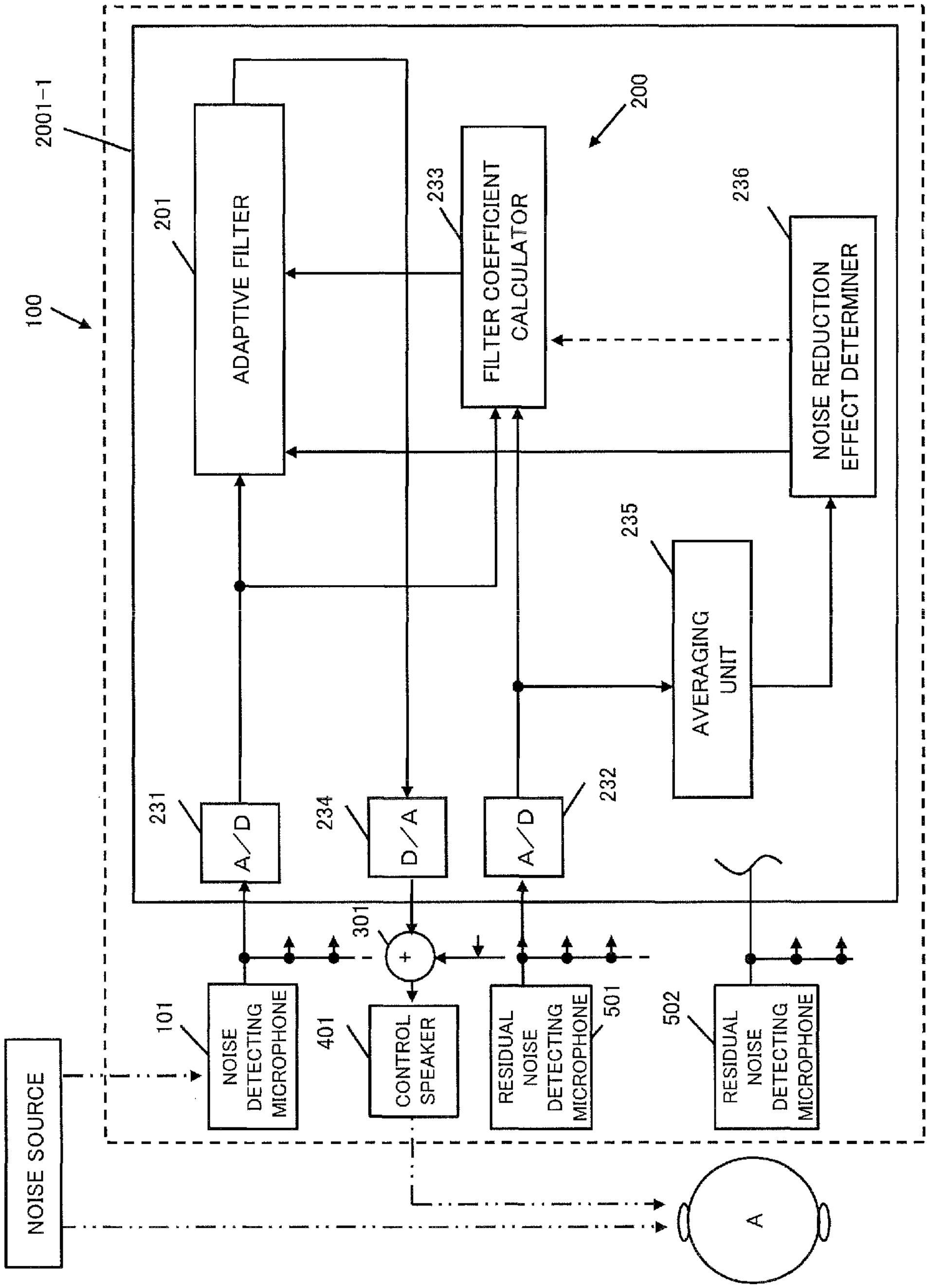
FIG. 3 is a block diagram illustrating a configuration of a noise controller of the noise reduction apparatus.

FIG. 3 is a block diagram illustrating the configurations of the noise controllers. The noise controllers 2001-1 to 2001-4, 2002-1 to 2002-4, 2020-1 to 2020-4 described with reference to FIG. 1 have the same internal circuit configuration. For this reason, the noise controller 2001-1 will be described below as an example. FIG. 3 illustrates the noise detecting microphone 101, the adder 301, the control speaker 401, and the residual noise detecting microphones 501 and 502 that are related to the noise controller 2001-1, out of the noise detecting microphones 101 to 120, the adders 301 to 304, the control speakers 401 to 404, and the residual noise detecting microphones 501 and 502. Since the configuration after the residual noise detecting microphone 501 is identical to the configuration after the residual noise detecting microphone 502, only the configuration after the residual noise detecting microphone 501 will be described.

The noise controller 2001-1 is provided with A/D converters 231 and 232, an adaptive filter 201, a filter coefficient calculator 233, a D/A converter 234, an averaging unit 235 and a noise reduction effect determiner 236. The A/D converters 231 and 232, the adaptive filter 201, the filter coefficient calculator 233, the D/A converter 234, the adder 301 and the control speaker 401 configure a control sound output unit 200.

The A/D converter 231 A/D-converts a noise signal from the noise detecting microphone 101, and outputs the converted signal to the adaptive filter 201 and the filter coefficient calculator 233.

The A/D converter 232 A/D converts a residual noise signal from the residual noise detecting microphone 501, and outputs the converted signal to the filter coefficient calculator 233 and the averaging unit 235.

The D/A converter 234 outputs the output from the adaptive filter 201 to the control speaker 401 via the adder 301.

The adaptive filter 201 is an FIR (Finite Impulse Response) filter. The FIR filter has a multistage tap, and can freely set filter coefficients of the respective taps.

The filter coefficient calculator 233 inputs a noise signal output from the noise detecting microphone 101 via the A/D converter 231, and a residual noise signal output from the residual noise detecting microphone 501 via the A/D converter 232. The filter coefficient calculator 233 obtains a filter coefficient for making a residual noise detected at the control point based on the noise signal and the residual noise signal minimum, and outputs the filter coefficient to the adaptive filter 201. Specifically, the filter coefficient calculator 233 obtains the filter coefficient for making the control speaker 401 to generate a control sound of which phase is opposite to that of noises from the noise sources on the installed position of the residual noise detecting microphone 501, and outputs the filter coefficient to the adaptive filter 201.

The averaging unit 235 averages level of the residual noise signal input from the residual noise detecting microphone 501. As a result, instant fluctuations in the level of the residual noise signal can be reduced. For example, the averaging unit 235 obtains an average value of the level of the residual noise signal for a predetermined time before and after a target time. The averaging unit 235 may carry out the averaging through another method.

The noise reduction effect determiner 236 calculates a noise reduction amount using the residual noise signal level averaged by the averaging unit 235, namely, the residual noise signal level from which an influence of the instant fluctuations is eliminated. For example, the noise reduction effect determiner 236 saves the residual noise signal level at the ANC/OFF time, and calculates a noise reduction amount at the ANC/ON time based on the residual noise signal level at the ANC/ON time, and the saved residual noise signal level at the ANC/OFF time. The noise reduction effect determiner 236 determines the noise reduction effect based on the noise reduction amount.

When the calculated noise reduction amount is a predetermined value or more, the noise reduction effect determiner 236 determines that the noise reduction effect is present, and instructs the adaptive filter 201 to continue the ANC operation (ANC/ON). On the contrary, when the calculated noise reduction amount is a predetermined value or less, the noise reduction effect determiner 236 determines that the noise reduction effect is not satisfactory, and instructs the adaptive filter 201 to stop the ANC operation (ANC/OFF).

For example, when the residual noise signal level detected by the residual noise detecting microphone 501 at the ANC/ON time is larger than the saved residual noise signal level the ANC/OFF time, it is considered that the residual noises increase due to ANC/ON. In this case, a shift to ANC/OFF can eliminate the increase in the residual noise level (an increase in noises), and thus uncomfortable feelings are not given to users.

2. Effect Obtained by Providing Averaging Unit

Figure 4B:
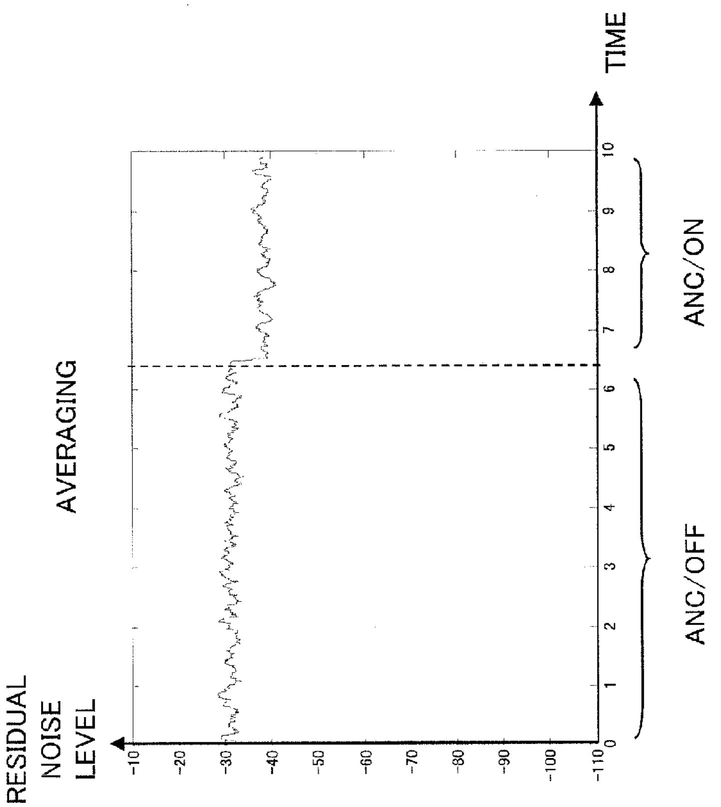
FIGS. 4A and 4B are explanatory diagrams illustrating an effect produced due to an averaging unit.
Figure 4A:
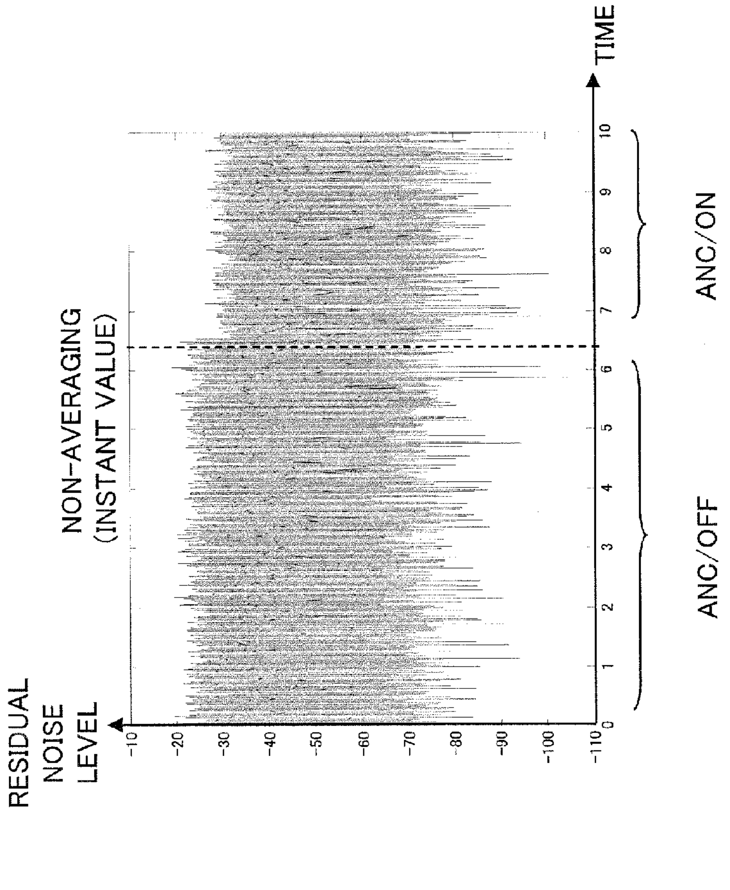

FIGS. 4A and 4B are explanatory diagrams illustrating the effect obtained by the averaging unit 235. Specifically, FIG. 4A is a diagram illustrating the residual noise level actually measured in a case where the averaging unit 235 is not provided, and FIG. 4B is a diagram illustrating the residual noise level actually measured in a case where the averaging unit 235 is provided (FIG. 4B). In the case where the averaging unit 235 is not provided and in the case where the averaging unit 235 is provided, the residual noise levels were measured at the ANC/OFF time and the ANC/ON time.

When the averaging unit 235 is not provided, as shown in FIG. 4A, the instant fluctuation in the noise level is large. For this reason, it is difficult to accurately estimate a difference between the noise levels at the ANC/OFF time and the ANC/ON time, namely, the noise reduction effect.

On the contrary, when the averaging unit 235 is provided as in the first embodiment, the instant fluctuation is nearly eliminated as shown in FIG. 4B. As a result, the difference between the noise levels at the ANC/OFF time and at the ANC/ON time, namely, the noise reduction amount (the noise reduction effect) can be accurately estimated.

Instead of the shift to ANC/OFF, parameters relating to the design of the filter coefficients may be changed to be re-optimized. The parameters relating to the design of the filter coefficients are, for example, a learning speed μ in the Filtered-X_LMS method. In this case, the noise reduction effect determiner 236 may output an instruction signal for changing and optimizing the parameters relating to the design of the filter coefficients to the filter coefficient calculator 233 as shown by a broken line in FIG. 3.

Instead of the shift to ANC/OFF, an updating amount of the filter coefficient to be output from the filter coefficient calculator 233 to the adaptive filter 201 is set to 0, so that the adaptive filter 201 can function as the fixed filter. In this case, the noise reduction effect determiner 236 may output an instruction signal for setting the updating amount of the filter coefficient to 0 as shown by the broken line in FIG. 3 to the filter coefficient calculator 233.

The first embodiment has described the case in which the noise level at the ANC/ON time is compared with the noise level at the ANC/OkF time, but the noise level at the ANC/ON time may be compared with a predetermined value. As a result, for example, only when the noise level at the ANC/ON time is very large, the state can be changed to the ANC/OFF. Alternatively, for example, when the noise level at the ANC/ON time is slightly large, namely, when the noise reduction effect is deteriorated only slightly, the state can be changed to ANC/OFF.

Second Embodiment

1. Configuration

Figure 5:
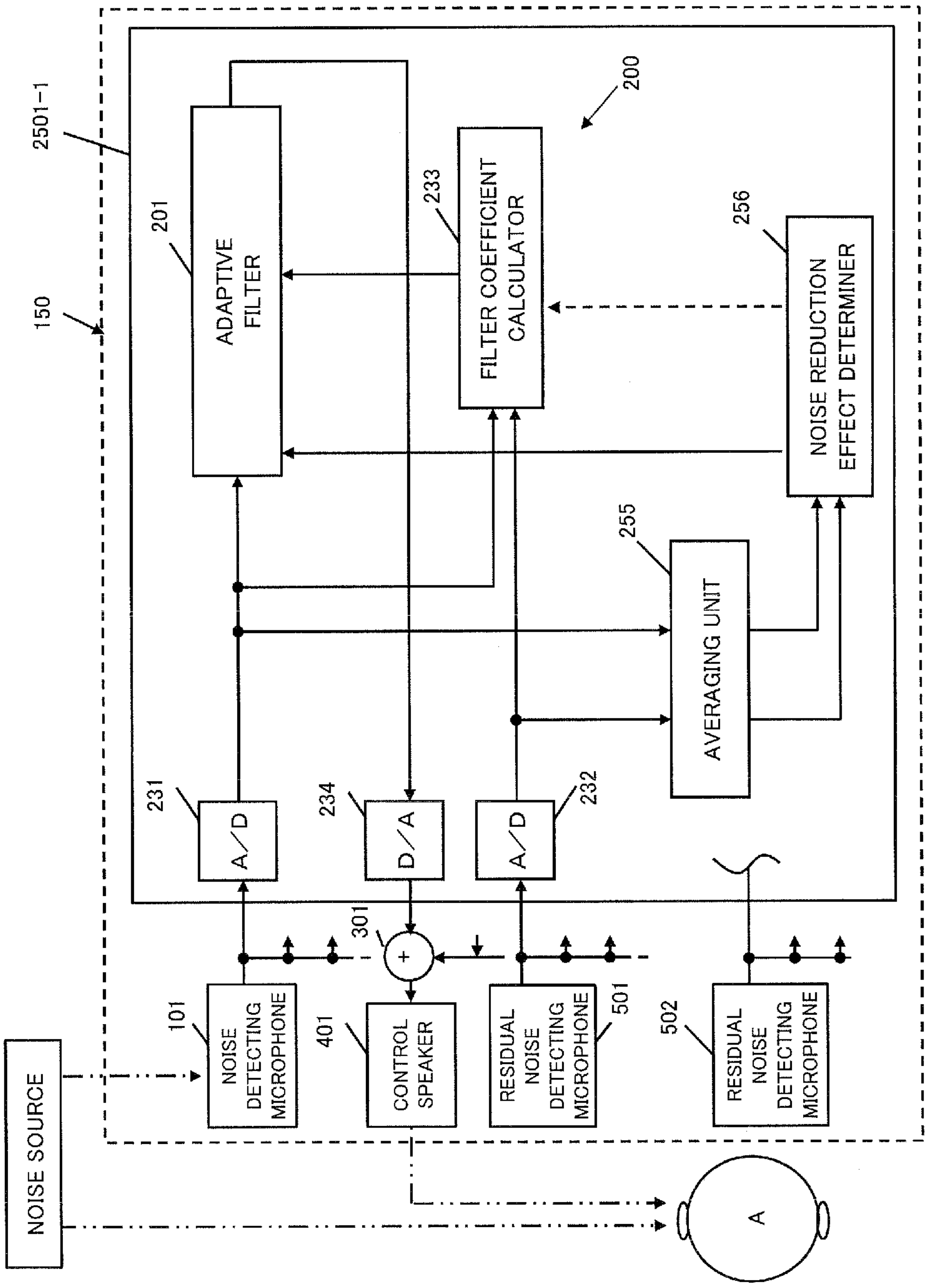
FIG. 5 is a block diagram illustrating a configuration of the noise controller of the noise reduction apparatus according to a second embodiment.

FIG. 5 is a block diagram illustrating a configuration of the noise controller of a noise reduction apparatus 150 according to a second embodiment.

The noise reduction apparatus 150 according to the second embodiment is provided with the noise controller 2501-1 instead of the noise controller 2001-1 of the noise reduction apparatus 100. The entire configuration of the noise reduction apparatus is similar to that in the first embodiment in FIGS. 2A to 2C, and in FIGS. 2A to 2C, the noise controllers 2501-1 to 2501-4, 2502-1 to 2502-4, . . . 2520-1 to 2520-4 are provided instead of the noise controllers 2001-1 to 2001-4, 2002-1 to 2002-4, . . . 2020-1 to 2020-4. Since the plurality of the noise controllers 2501-1 to 2501-4, 2502-1 to 2502-4, . . . 2520-1 to 2520-4 have the same configuration in the internal circuit, the noise controller 2501-1 will be described below as an example. FIG. 5 illustrates the noise detecting microphone 101, the adder 301, the control speaker 401, and the residual noise detecting microphone 501 that are related to the noise controller 2501-1, out of the noise detecting microphones 101 to 120, the adders 301 to 304, the control speakers 401 to 404, and the residual noise detecting microphones 501 and 502 shown in FIGS. 2A to 2C.

In the noise controller 2501-1 according to the second embodiment, the noise signal from the noise detecting microphone 101 is input into an averaging unit 255 via the A/D converter 231. The signal averaged by the averaging unit 255 is input into a noise reduction effect determiner 256. The noise reduction effect determiner 256 determines the noise reduction effect based on the noise signal from the noise detecting microphone 101 and the residual noise signal from the residual noise detecting microphone 501.

Figure 6A:
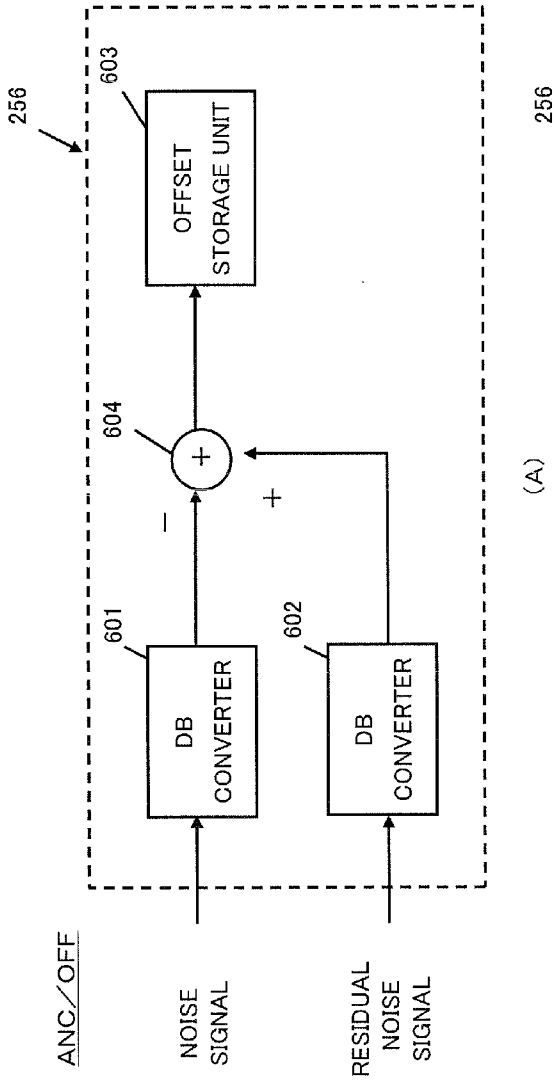
FIGS. 6A and 6B are block diagrams illustrating a configuration of a noise reduction effect determiner of the noise reduction apparatus.
Figure 6B:
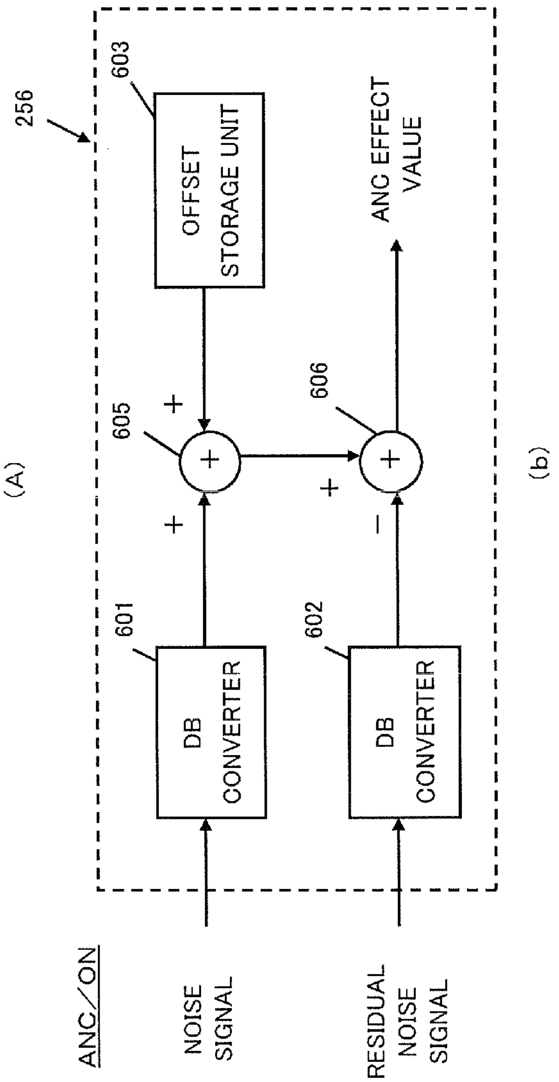

FIGS. 6A and 6B are block diagrams illustrating a configuration of the noise reduction effect determiner 256 according to the second embodiment. The noise reduction effect determiner 256 can switch the circuit configuration between the ANC/OFF and the ANC/ON. FIG. 6A illustrates the circuit configuration at the ANC/OFF time, and FIG. 6B illustrates the circuit configuration at the ANC/ON time.

As shown in FIG. 6A, at the ANC/OFF time, the noise reduction effect determiner 256 has dB converters 601 and 602, an adder 604, and an offset storage unit 603. The dB converter 601 converts the level of the noise signal averaged by the averaging unit 255 into a dB value (decibel value, the noise level) to output the dB value. The dB converter 602 converts the level of the residual noise signal averaged by the averaging unit 255 into a dB value to output the dB value. The adder 604 adds a value obtained by inverting an output from the dB converter 601 to an output from the dB converter 602 to output the added value. The offset storage unit 603 stores an output from the adder 604. That is, the adder 604 outputs a level (offset value) of a difference between the noise level and the residual noise level.

On the contrary, at the ANC/ON time, the noise reduction effect determiner 256 includes the dB converters 601 and 602, the adders 605 and 606, and the offset storage unit 603 as shown in FIG. 6B. The dB converter 601 converts a level of a noise detection signal averaged by the averaging unit 255 into a dB value to output the dB value. The dB converter 601 converts a level of a noise signal averaged by the averaging unit 255 into a dB value to output the dB value. The adder 604 adds an output from the dB converter 601 and an output from the offset storage unit 603 to output the added value. The offset storage unit 603 outputs an offset value stored at the ANC/OFF time. In the adder 605, the value obtained by adding the output from the dB converter 601 and the output from the offset storage unit 603 becomes an estimated value of the level of the noise (estimated noise level) detected by the residual noise detecting microphone in the OFF state of ANC. The adder 606 outputs a value obtained by adding the value obtained by inverting the output from the dB converter 602, and the output from the adder 604. In the adder 606, a value, which is obtained by adding a value obtained by inverting the output from the dB converter 602 (residual noise detection signal estimated value) and a value obtained by inverting the output from the dB converter 602, becomes a noise reduction value by means of ANC/ON. The noise reduction effect determiner 256 determines the noise reduction effect based on the noise reduction value.

2. Noise Reduction Effect at the Time of Noise Fluctuation

In order to accurately determine the noise reduction effect, even when the levels of the noises generated from the noise sources fluctuate, a difference between the noise level detected by the noise detecting microphone 101 and the noise level detected by the residual noise detecting microphone 501 should not be changed.

Figure 7:
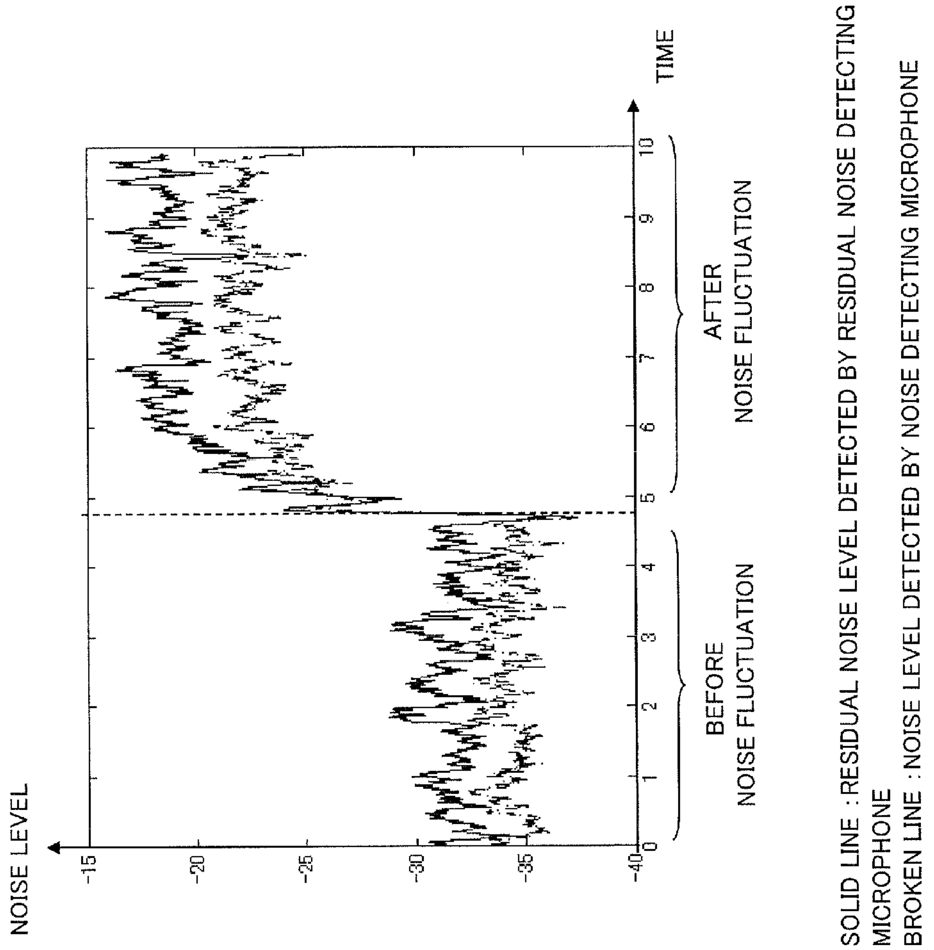
FIG. 7 is a diagram illustrating a time change in a noise level in aircraft.

FIG. 7 is a diagram illustrating a time change in the noise level in aircraft. In FIG. 7, a vertical axis represents the noise level (dB), and a horizontal axis represents time (second). A solid line in FIG. 7 indicates the noise level that is detected by the residual noise detecting microphone 501 and is output from the dB converter 602, and a broken line indicates the noise level that is detected by the noise detecting microphone 101 and is output from the dB converter 602.

As shown in FIG. 7, it is found that the difference between the noise level and the residual noise level after the noise fluctuation is approximately the same as the difference between the noise level and the residual noise level before the noise fluctuation. This is considered to be because the noises generated in the aircraft are reflected from walls and shell inside the aircraft and are averaged as a result. That is, a fluctuation in the noises in the aircraft does not locally occur and occurs in a wide range. In this example, a case where noises increase is described, but much the same is true on a case where noises are reduced.

Figure 8:
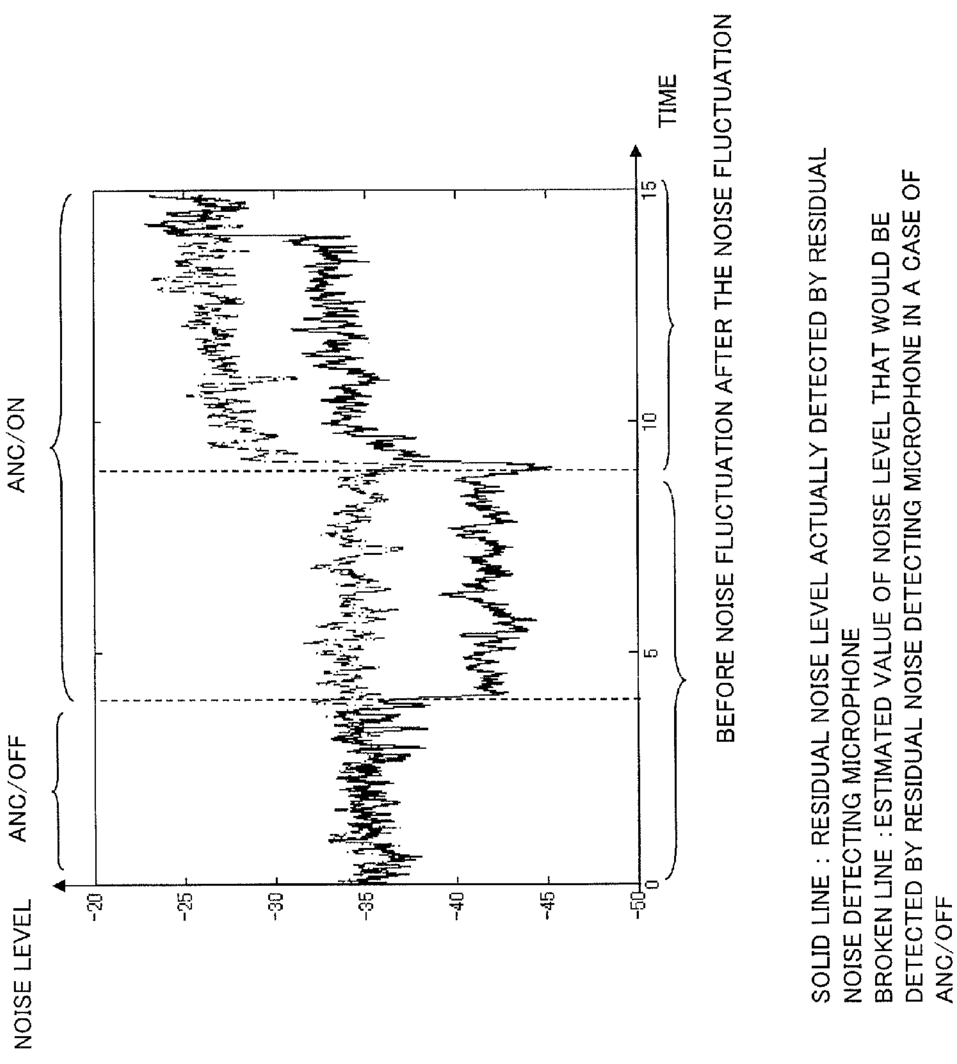
FIG. 8 is a diagram describing an effect of the noise reduction effect determiner in the noise reduction apparatus.

3. Effect Obtained by Noise Reduction Effect Determiner According to Second Embodiment FIG. 8 is a diagram for describing the effect obtained by the noise reduction effect determiner 256 according to the second embodiment. A solid line in FIG. 8 indicates the level of noises actually detected by the residual noise detecting microphone 501 (hereinafter, suitably referred to as "the actual noise level"). A broken line in FIG. 8 indicates an estimated value of the noise level (hereinafter, suitably referred to as "the estimated noise level") that would be detected by the residual noise detecting microphone 501 in a case of ANC/OFF. A difference between the actual noise level and the estimated noise level becomes the noise reduction amount at the ANC/ON time.

As shown in FIG. 8, at the ANC/OFF time, the actual noise level actually detected by the residual noise detecting microphone and the estimated noise level have approximately the same values. This represents that the noise level is satisfactorily estimated by the noise reduction effect determiner 256 at the ANC/OFF time. In this state, the shift to ANC/ON reduces the actual noise level (residual noise level) actually detected by the residual noise detecting microphone 501. The difference between the residual noise level and the estimated noise level becomes the noise reduction amount.

When the level of the noises generated from the noise sources rises at the ANC/ON time, the actual noise level actually detected by the residual noise detecting microphone 501 rises. In the second embodiment, the estimated noise level is estimated based on the actual noise level detected by the noise detecting microphone 101, but the actual noise level actually detected by the residual noise detecting microphone 501 and the actual noise level actually detected by the noise detecting microphone 101 fluctuate with approximately constant offset values as described with reference to FIG. 7. For this reason, the shift to ANC/ON enables the estimated noise level detected by the residual noise detecting microphone 501 to be accurately estimated. Therefore, even when the levels of the noises generated from the noise sources fluctuate, the estimated noise levels can be accurately estimated. That is, the noise reduction amount can be accurately estimated whether it is before or after the noise fluctuation.

In the first embodiment, when the levels of the noises from the noise sources change, a defective operation might be performed. For example, when the levels of the noises from the noise sources are large, even if the noise reduction apparatus 100 normally operates, the residual noise after the noise reduction is occasionally louder than the saved noises at the ANC/OFF time. In this case, determination is erroneously made that the noises increase due to the shift to ANC/ON. However, in the second embodiment, the estimated noise level changes according to the levels of the noises from the noise sources. Thus, this problem can be solved.

In order to simplify the description, the case where one noise detecting microphone and one residual noise detecting microphone are provided has been described, but the same effect can be also obtained in a case where a plurality of each of microphones are provided.

4. Conclusion (Configuration, Effect, and the like)

In the second embodiment, the noise reduction apparatus 150 includes:

the noise detecting microphone 101 (a first noise detecting microphone) for detecting noises on a position different from a noise reduction target position;

the residual noise detecting microphone 501 (a second noise detecting microphone) for detecting noises on the noise reduction target position;

the control sound output unit 200 (a control sound output unit) for generating a control sound for reducing the noises on the noise reduction target position, based on an output from the noise detecting microphone 101 and an output from the residual noise detecting microphone 501 to output the control sound; and the noise reduction effect determiner 256 (a noise reduction amount calculator) for calculating a reduction amount of the noises on the noise reduction target position, based on the output from the noise detecting microphone 101 and the output from the residual noise detecting microphone 501, wherein the noise reduction effect determiner 256 includes

- the adder 604 (a difference calculator) for obtaining a difference between the noise level detected by the noise detecting microphone 101 and the noise level detected by the residual noise detecting microphone 501 in a state where the control sound output unit 200 does not output a control sound,
- the offset storage unit 603 (a storage unit) for storing the difference calculated by the adder 604,
- the adder 605 (an estimated noise value calculator) for estimating the noise level that is to be detected by the residual noise detecting microphone 501 in the state where the control sound output unit 200 does not output the control sound, based on the noise level detected by the noise detecting microphone 101 in a state where the control sound output unit 200 outputs the control sound and the difference stored in the offset storage unit 603, and
- the adder 606 (a reduction amount calculator) for calculating the noise reduction amount on the noise reduction target position, based on the estimated noise value calculated by the adder 605 and the level of the residual noise detected by the residual noise detecting microphone 501 in a state where the control sound output unit 200 outputs the control sound.

Accordingly, when obtaining the noise reduction amount on the noise reduction target position, the noise reduction apparatus 150 does not have to be stopped. For this reason, an uncomfortable feeling given to the user can be reduced.

In the second embodiment, the noise reduction apparatus 150 includes the noise reduction effect determiner 256 (a noise controller) for controlling an output state of the control sound in the control sound output unit 200 based on the noise reduction amount calculated by the noise reduction effect determiner 256.

Accordingly, the output state of the control sound in the control sound output unit 200 is controlled based on the noise reduction amount. For this reason, for example, when the noises detected by the residual noise detecting microphone 501 are louder than the noises detected by the noise detecting microphone 101, the output of the control sound can be stopped.

In the noise reduction apparatus 150 according to the second embodiment, when the noise reduction amount calculated by the noise reduction effect determiner 256 (noise reduction amount calculator) is equal to or less than a threshold, the noise reduction effect determiner 256 (a noise controller) instructs the control sound output unit 200 to stop output of a control sound.

Accordingly, when the noise reduction amount is equal to or less than the threshold, the output of the control sound is stopped. For this reason, the output of the control sound can be reliably stopped.

In the noise reduction apparatus 150 according to the second embodiment, the control sound output unit 200 can change a characteristic of the control sound, and when the noise reduction amount calculated by the noise reduction effect determiner 256 (noise reduction amount calculator) is equal to or less than the threshold, the noise reduction effect determiner 256 (the noise controller) may instruct the control sound output unit 200 to change the characteristic of the output control sound.

Accordingly, when the noise reduction amount is equal to or less than the threshold, the output of the control sound is stopped. For this reason, the output of the control sound can be reliably stopped.

In the second embodiment, the noise reduction apparatus 150 further includes the averaging unit 255 (a fluctuation suppressing unit) for absorbing an instant fluctuation in the outputs from the noise detecting microphone 101 and the residual noise detecting microphone 501, and then outputting the outputs from the noise detecting microphone 101 and the residual noise detecting microphone 501.

Accordingly, the outputs from the noise detecting microphone 101 and the residual noise detecting microphone 501 are input into the noise reduction effect determiner 256 of which instant fluctuation is absorbed. For this reason, calculating accuracy of the noise reduction amount is improved.

In the noise reduction apparatus 150 according to the second embodiment, the averaging unit 255 averages the outputs from the noise detecting microphone 101 and the residual noise detecting microphone 501 in a time region.

Accordingly, the outputs from the noise detecting microphone 101 and the residual noise detecting microphone 501 are averaged in the time region. For this reason, the instant fluctuation can be absorbed. Therefore, the calculating accuracy of the noise reduction amount is improved.

The fluctuation suppressing unit may be a low-pass filter that allows components in a predetermined frequency range on a low range side of the outputs from the noise detecting microphone 101 and the residual noise detecting microphone 501 to pass.

Accordingly, the outputs from the noise detecting microphone 101 and the residual noise detecting microphone 501 in the predetermined frequency range on the low range side pass. That is, components in a frequency range of a high range side do not pass or the passing is suppressed. For this reason, the instant fluctuation can be absorbed. Therefore, the calculating accuracy of the noise reduction amount is improved.

Another Embodiment

The first and second embodiments have been described as the examples of the technique disclosed in the present application. However, the technique in this disclosure is not limited thereto, and the present disclosure can be applied also to embodiments where modifications, replacements, addition, and omission are carried out. Further, the components described in the first and second embodiments may be combined to provide a new embodiment.

The first and second embodiments have described the case where one noise controller is connected to one noise detecting microphone 101. However, a plurality of noise detecting microphones may be provided. In this case, the fluctuation suppressing unit calculates an average value of the outputs from the plurality of noise detecting microphones, and the calculated average value may be used as the outputs from the noise detecting microphones. In this case, the average value of the outputs from the plurality of noise detecting microphones can be used as outputs from the noise detecting microphones. Such a configuration improves the estimating accuracy of the noise levels on the positions of the residual noise detecting microphones.

In the second embodiment, the levels of the noise signals from the noise sources and the level of the residual noise signal detected by the residual noise detecting microphone are converted into dB values (the noise levels), and the value obtained by adding the dB values is used as an offset value. This offset value is added to the current noise level, so that the estimated noise level is obtained, but the present disclosure is not limited thereto. For example, the levels of the residual noise signals detected by the noise detecting microphone 101 and the residual noise detecting microphone 501 are not converted into dB values (the noise levels), but the estimated noise levels may be obtained. For example, a ratio of the levels of the residual noise signals (linear values) detected by the noise detecting microphone 101 and the residual noise detecting microphone 501 is obtained, and the current residual noise level is multiplied by this ratio, so that the estimated noise level may be obtained.

Figure 9:
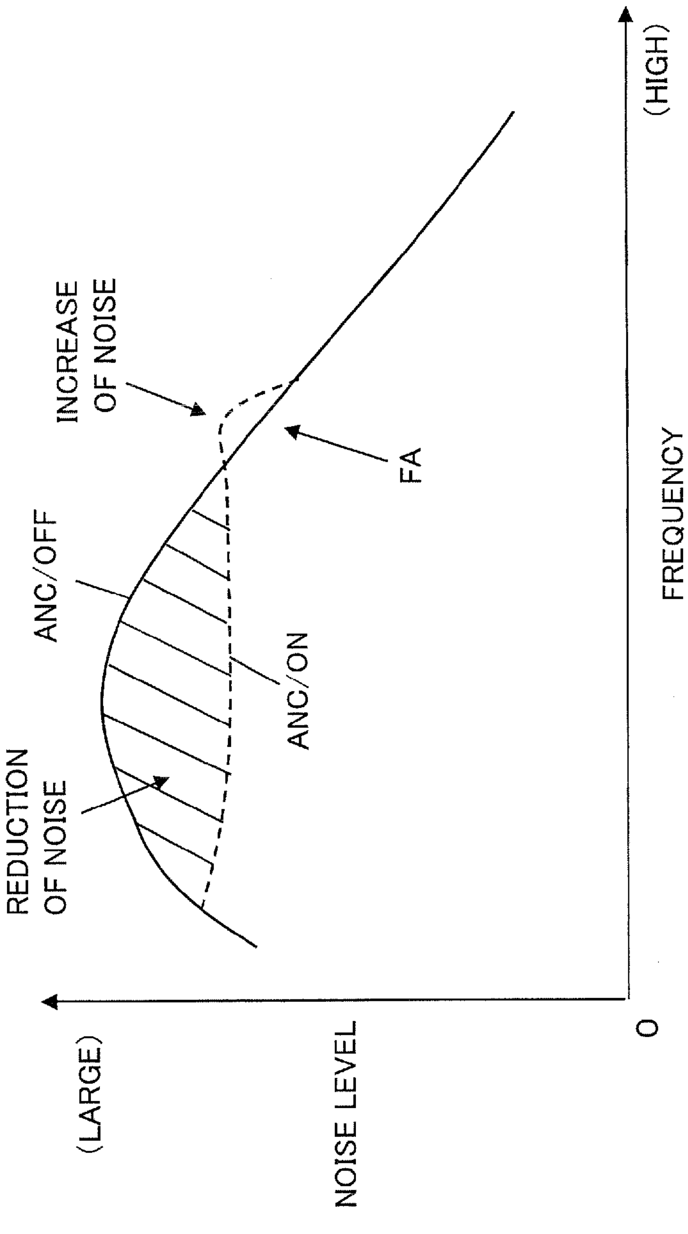
FIG. 9 is a diagram describing an effect of the noise reduction apparatus according to another embodiment.

The levels of the noises from the noise sources and the frequency band of the residual noise detected by the residual noise detecting microphone are divided into a plurality of frequency bands, and the noise level and the residual noise level are obtained in each of the frequency bands, so that the noise reduction amount may be obtained in each of the frequency band. FIG. 9 is a diagram for describing an effect of this configuration. A solid line of FIG. 9 indicates the level of the residual noise signal at the ANC/OFF time, and a broken line indicates the level of the residual noise signal at the ANC/ON time. In the example of FIG. 9, in a middle-low tone range, the level of the residual noise signal at the ANC/ON time is lower than the level of the residual noise signal at the ANC/OFF time. As a result, the noise reduction effect is obtained. However, in a partial frequency band on the high-tone side (a range shown by Fa), the level of the residual noise signal at the ANC/ON time is higher than the level of the noise signal at the ANC/OFF time. As a result, the noise reduction effect is not obtained. When the partial frequency band on the high-tone side includes a frequency band in which the human's sense of hearing is sensitive, a user may have an uncomfortable feeling at the ANC/ON time. However, when the frequency band is not divided and the noise reduction effect is determined, namely, when the noise reduction effect is determined by averaging an entire frequency band, and the determination is made that the noise reduction effect is obtained, ANC/OFF is not carried out. That is, a state where the user has an uncomfortable feeling continues. However, when the frequency band is divided and the noise reduction effect is determined as in this example, ANC/OFF can be carried out when the noise reduction effect is not obtained in the frequency band in which the human's sense of hearing is sensitive. As a result, the user can be prevented from having the uncomfortable feeling.

The effect of ANC may be visually carried to the user by displaying the noise reduction amount (the noise reduction effect) on a monitor. For example, when a monitor for viewing movies mounted onto a seat in aircraft is used, the noise reduction effect can be visually carried to the users while a great increase in cost is suppressed.

The embodiments have been described as the examples of the technique in this disclosure. For this reason, the accompanying drawings and the detailed description are provided.

Therefore, the components illustrated in the accompanying drawings and described in the detailed description include not only the components required for solving the problem but also the components that are not required for solving the problem in order to illustrate the above technique. For this reason, even if such unrequired components are illustrated in the accompanying drawings and described in the detailed description, these unrequired components should not be immediately regarded as necessary.

Since the above embodiments are for illustrating the technique in the disclosure, various alternations, replacements, additions, and omissions can be carried out within the scope of claims and an equivalent scope.

INDUSTRIAL APPLICABILITY

The noise reduction apparatus of the present disclosure can be applied to the noise reduction apparatus for reducing noises on the noise reduction target position. Specifically, the present disclosure can be applied to the noise reduction apparatus that is used in spaces such as aircraft, trains, and automobiles that require high comfortability in complicated noise environments.

What is claimed is:

1. A noise reduction apparatus, comprising:

a first noise detecting microphone operable to detect a noise on a position different from a noise reduction target position;

a second noise detecting microphone operable to detect a noise on the noise reduction target position;

a control sound output unit operable to generate a control sound for reducing the noise on the noise reduction target position based on an output from the first noise detecting microphone and an output from the second noise detecting microphone to output the control sound; and a noise reduction amount calculator operable to calculate a reduction amount of the noise on the noise reduction target position based on the output from the first noise detecting microphone and the output from the second noise detecting microphone, wherein the noise reduction amount calculator includes a first calculator operable to obtain a difference between a level of the noise detected by the first noise detecting microphone and a level of the noise detected by the second noise detecting microphone in a state where the control sound output unit does not output the control sound, a storage unit operable to store the difference calculated by the first calculator, a second calculator operable to estimate a noise level that is to be detected by the second noise detecting microphone in the state where the control sound output unit does not output the control sound, based on the level of the noise detected by the first noise detecting microphone in a state where the control sound output unit outputs the control sound and the difference stored in the storage unit, and a third calculator operable to calculate a noise reduction amount on the noise reduction target position, based on the estimated noise value calculated by the second calculator and the level of the noise detected by the second noise detecting microphone in the state where the control sound output unit outputs the control sound.

2. The noise reduction apparatus according to claim 1, further comprising a noise controller operable to control an output state of the control sound in the control sound output unit based on the noise reduction amount calculated by the noise reduction amount calculator.

3. The noise reduction apparatus according to claim 2, wherein, when the noise reduction amount calculated by the noise reduction amount calculator is equal to or less than a threshold, the noise controller instructs the control sound output unit to stop output of the control sound.

4. The noise reduction apparatus according to claim 2, wherein the control sound output unit can change a characteristic of the control sound, the noise controller instructs the control sound output unit to change the characteristic of the control sound to be output when the noise reduction amount calculated by the noise reduction amount calculator is equal to or less than the threshold.

5. The noise reduction apparatus according to claim 1, further comprising a fluctuation suppressing unit operable to suppress an instant fluctuation in the outputs from the first noise detecting microphone and the second noise detecting microphone and output the outputs of which instant fluctuation is suppressed as the outputs from the first noise detecting microphone and the second noise detecting microphone.

6. The noise reduction apparatus according to claim 5, wherein the fluctuation suppressing unit is a low-pass filter that allows components in a predetermined frequency range in the outputs from the first noise detecting microphone and the second noise detecting microphone to pass.

7. The noise reduction apparatus according to claim 5, wherein the fluctuation suppressing unit is an averaging unit that averages the outputs from the first noise detecting microphone and the second noise detecting microphone in a time region.

8. The noise reduction apparatus according to claim 5, wherein the first noise detecting microphone includes a plurality of noise detecting microphones, the fluctuation suppressing unit calculates an average value of noise levels detected by the plurality of the noise detecting microphones, and uses the calculated average value as the level of the noise detected by the first noise detecting microphone.

9. The noise reduction apparatus according to claim 1, further comprising a video output device operable to display information about the noise reduction amount output from the noise reduction amount calculator.

* * * * *